United States Patent
DeRemer et al.

(10) Patent No.: US 9,028,404 B2
(45) Date of Patent: May 12, 2015

(54) PHYSIOLOGICAL STATUS MONITORING SYSTEM

(75) Inventors: Matthew J. DeRemer, Allston, MA (US); Richard B. Streeter, Andover, MA (US); Craig D. Mielcarz, Somerville, MA (US); Gordon S. Lewis, Needham, MA (US); David McDonald, Medway, MA (US)

(73) Assignee: Foster-Miller, Inc., Waltham, MA (US)

( * ) Notice: Subject to any disclaimer, the term of this patent is extended or adjusted under 35 U.S.C. 154(b) by 354 days.

(21) Appl. No.: 12/804,761

(22) Filed: Jul. 28, 2010

(65) Prior Publication Data

US 2012/0029299 A1 Feb. 2, 2012

(51) Int. Cl.
*A61B 5/00* (2006.01)
*G06F 13/00* (2006.01)
*A61B 5/02* (2006.01)
(Continued)

(52) U.S. Cl.
CPC ............... *A61B 5/6805* (2013.01); *A61B 5/02* (2013.01); *H05K 1/18* (2013.01); *A61B 5/0002* (2013.01); *A61B 5/02438* (2013.01); *A61B 5/0816* (2013.01); *A61B 5/1118* (2013.01); *A61B 5/6831* (2013.01)

(58) Field of Classification Search
CPC .... A61B 5/6801–5/6804; A61B 5/11–5/1118; A61B 5/0002; A61B 5/02; A41D 13/1236–13/1281; H05K 1/18–1/189; H05K 5/0004–5/0013; H01R 12/70; H01R 12/771–12/79; H01R 12/716; E05B 9/002–9/10
USPC ................. 600/300–301, 306–309, 372–374, 600/382–384, 386–394, 481–484, 500–503, 600/508–509, 513–519, 529–531, 533–538, 600/549, 587; 2/1, 455–458, 2.11, 2.12, 2/2.13, 2.15, 2.16, 2.17, 459, 462, 463, 2/464, 410, 69, 171
See application file for complete search history.

(56) References Cited

U.S. PATENT DOCUMENTS 2,021,111 A 11/1935 Wheat
2,953,970 A 9/1960 Maynard
(Continued)

FOREIGN PATENT DOCUMENTS

DE 103 06 953 A1 10/2003
EP 0320901 A2 6/1989
(Continued)

OTHER PUBLICATIONS

Shaw, G. A. et al; "Warfighter Physiological and Environmental Monitoring: A Study for the U.S. Army Research Institute in Environmental Medicine and the Soldier Systems Center", Lincoln Laboratory, MIT, Nov. 2004, p. 1-141.*

(Continued)

*Primary Examiner* — William Thomson
*Assistant Examiner* — Marie Archer
(74) *Attorney, Agent, or Firm* — Iandiorio Teska & Coleman, LLP (57) ABSTRACT

A physiological monitoring system includes a sensor subsystem worn by a person including at least a one sensor. A dock is associated with the sensor subsystem and includes a first connector component electrically connected to the sensor. A portable transmitting unit is received in the dock and includes a transmitter and a connector component removeably mateable with the dock connector component to route sensor data to the transmitter.

15 Claims, 9 Drawing Sheets

(51) Int. Cl.
 *A61B 5/024* (2006.01)
 *A61B 5/08* (2006.01)
 *A61B 5/11* (2006.01)
 *H05K 1/18* (2006.01)

(56) References Cited

U.S. PATENT DOCUMENTS

| | | |
|---|---|---|
| 2,963,535 A | 12/1960 | Wegener et al. |
| 2,963,538 A | 12/1960 | Dahlgren |
| 2,997,521 A | 8/1961 | Dahlgren |
| 3,086,071 A | 4/1963 | Preston |
| 3,229,030 A | 1/1966 | Baermann |
| 3,247,755 A | 4/1966 | Siegmund |
| 3,288,175 A | 11/1966 | Valko |
| 3,371,250 A | 2/1968 | Ross et al. |
| 3,414,666 A | 12/1968 | Doundoulakis et al. |
| 3,447,120 A | 5/1969 | Rask et al. |
| 3,473,872 A | 10/1969 | Okamura |
| 3,476,870 A | 11/1969 | Ross |
| 3,479,565 A | 11/1969 | Ross et al. |
| 3,495,025 A | 2/1970 | Ross |
| 3,507,321 A | 4/1970 | Palma |
| 3,551,585 A | 12/1970 | Smart et al. |
| 3,627,903 A | 12/1971 | Plummer |
| 3,631,298 A | 12/1971 | Davis |
| 3,654,380 A | 4/1972 | Tatum et al. |
| 3,700,538 A | 10/1972 | Kennedy |
| 3,711,627 A | 1/1973 | Maringulov |
| 3,778,331 A | 12/1973 | Scharf |
| 3,878,316 A | 4/1975 | Groff |
| 3,882,846 A | 5/1975 | Fletcher et al. |
| 3,891,011 A | 6/1975 | Tisdale et al. |
| 3,909,508 A | 9/1975 | Ross |
| 3,926,360 A | 12/1975 | Moister, Jr. |
| 3,984,622 A | 10/1976 | Ross |
| 4,031,284 A | 6/1977 | Ingraham |
| 4,034,150 A | 7/1977 | Burnett, III |
| 4,035,694 A | 7/1977 | Barton et al. |
| 4,095,042 A | 6/1978 | Ross |
| 4,103,102 A | 7/1978 | Klein |
| 4,106,677 A | 8/1978 | Helmso et al. |
| 4,111,510 A | 9/1978 | Zurcher |
| 4,143,236 A | 3/1979 | Ross et al. |
| 4,145,030 A | 3/1979 | Ingraham |
| 4,150,464 A | 4/1979 | Tracy |
| 4,158,103 A | 6/1979 | Danilin et al. |
| 4,158,104 A | 6/1979 | Ross |
| 4,159,394 A | 6/1979 | Ross |
| 4,171,555 A | 10/1979 | Bakker et al. |
| 4,191,800 A | 3/1980 | Holtzman |
| 4,196,355 A | 4/1980 | Maine |
| 4,227,520 A | 10/1980 | Lord |
| 4,229,615 A | 10/1980 | Orr, Jr. et al. |
| 4,249,267 A | 2/1981 | Voss |
| 4,254,951 A | 3/1981 | DeLaney |
| 4,281,211 A | 7/1981 | Tatum et al. |
| 4,281,237 A | 7/1981 | Berenson |
| 4,370,658 A | 1/1983 | Hill |
| 4,373,534 A | 2/1983 | Watson |
| 4,430,384 A | 2/1984 | George |
| 4,442,314 A | 4/1984 | Piper |
| 4,452,847 A | 6/1984 | Siemon |
| 4,460,803 A | 7/1984 | Piper |
| 4,463,323 A | 7/1984 | Piper |
| 4,504,696 A | 3/1985 | Piper |
| 4,513,055 A | 4/1985 | Leibowitz |
| 4,527,135 A | 7/1985 | Piper |
| 4,550,411 A | 10/1985 | Stonestreet et al. |
| 4,559,411 A | 12/1985 | Piper |
| 4,572,197 A | 2/1986 | Moore et al. |
| 4,590,623 A | 5/1986 | Kitchman |
| 4,658,089 A | 4/1987 | Guzy et al. |
| 4,670,351 A | 6/1987 | Keane et al. |
| 4,682,828 A | 7/1987 | Piper et al. |
| 4,684,762 A | 8/1987 | Gladfelter |

| | | | |
|---|---|---|---|
| 4,709,397 A | 11/1987 | Voshall et al. | |
| 4,712,298 A | 12/1987 | Mondor, III | |
| 4,723,925 A | 2/1988 | Orr, Jr. et al. | |
| 4,735,847 A | 4/1988 | Fujiwara et al. | |
| 4,741,707 A | 5/1988 | Mondor, III | |
| 4,746,769 A | 5/1988 | Piper | |
| 4,753,088 A | 6/1988 | Harrison et al. | |
| 4,761,005 A | 8/1988 | French et al. | |
| 4,774,434 A | 9/1988 | Bennion | |
| 4,784,162 A * | 11/1988 | Ricks et al. | 600/484 |
| 4,803,096 A | 2/1989 | Kuhn et al. | |
| 4,804,806 A | 2/1989 | Orr, Jr. et al. | |
| 4,807,640 A | 2/1989 | Watson et al. | |
| 4,808,771 A | 2/1989 | Orr, Jr. | |
| 4,814,585 A | 3/1989 | Klein | |
| 4,815,473 A | 3/1989 | Watson et al. | |
| 4,817,625 A | 4/1989 | Miles | |
| 4,827,943 A | 5/1989 | Bornn et al. | |
| 4,851,613 A | 7/1989 | Jacques | |
| 4,854,446 A | 8/1989 | Strader | |
| 4,856,837 A | 8/1989 | Hammersla, Jr. | |
| 4,868,565 A | 9/1989 | Mettes et al. | |
| 4,875,144 A | 10/1989 | Wainwright | |
| 4,877,646 A | 10/1989 | Kuhn et al. | |
| 4,910,358 A | 3/1990 | Mittelbusher | |
| 4,912,611 A | 3/1990 | Lyle | |
| 4,913,978 A | 4/1990 | Klotz et al. | |
| 4,930,517 A | 6/1990 | Cohen et al. | |
| 4,948,951 A | 8/1990 | Balzano | |
| 4,960,118 A | 10/1990 | Pennock | |
| 4,983,452 A | 1/1991 | Daimon et al. | |
| 4,992,335 A | 2/1991 | Guerra et al. | |
| 5,008,517 A | 4/1991 | Brekkestran et al. | |
| 5,032,705 A | 7/1991 | Batcheller et al. | |
| 5,047,788 A | 9/1991 | Gillard | |
| 5,073,984 A | 12/1991 | Tone et al. | |
| 5,076,801 A | 12/1991 | Schroll | |
| 5,089,669 A | 2/1992 | Piper et al. | |
| 5,095,628 A | 3/1992 | McKenney et al. | |
| 5,103,504 A | 4/1992 | Dordevic | |
| 5,104,726 A | 4/1992 | Ross | |
| 5,119,020 A | 6/1992 | Massey et al. | |
| 5,126,920 A | 6/1992 | Cardashian et al. | |
| 5,140,131 A | 8/1992 | Macher et al. | |
| 5,191,893 A | 3/1993 | Reiten | |
| 5,203,717 A | 4/1993 | Beck et al. | |
| 5,216,732 A * | 6/1993 | Knott | 385/59 |
| 5,241,300 A | 8/1993 | Buschmann | |
| 5,259,792 A | 11/1993 | Beck et al. | |
| 5,277,617 A | 1/1994 | Shasteen | |
| 5,295,490 A | 3/1994 | Dodakian | |
| 5,301,678 A | 4/1994 | Watson et al. | |
| 5,316,830 A | 5/1994 | Adams, Jr. et al. | |
| 5,318,845 A | 6/1994 | Tanaka et al. | |
| 5,331,115 A | 7/1994 | Ysbrand | |
| 5,332,869 A | 7/1994 | Hagiwara | |
| 5,342,204 A | 8/1994 | Och | |
| 5,348,008 A * | 9/1994 | Bornn et al. | 600/301 |
| 5,353,793 A * | 10/1994 | Bornn | 600/386 |
| 5,357,593 A | 10/1994 | Bossler | |
| 5,362,656 A | 11/1994 | McMahon | |
| 5,371,326 A | 12/1994 | Clearwaters-Dreager et al. | |
| 5,373,103 A | 12/1994 | Orr, Jr. et al. | |
| 5,380,954 A | 1/1995 | Orr, Jr. | |
| 5,387,113 A | 2/1995 | Dickerson et al. | |
| 5,393,928 A | 2/1995 | Cribb et al. | |
| 5,415,561 A * | 5/1995 | Mavrin et al. | 439/341 |
| 5,416,310 A * | 5/1995 | Little | 235/462.44 |
| 5,457,610 A | 10/1995 | Bernardoni et al. | |
| 5,499,927 A | 3/1996 | Ohno et al. | |
| 5,502,631 A | 3/1996 | Adachi | |
| 5,523,528 A | 6/1996 | Bese et al. | |
| 5,531,405 A | 7/1996 | Goldberg | |
| 5,532,429 A | 7/1996 | Dickerson et al. | |
| 5,538,781 A | 7/1996 | Rao et al. | |
| 5,543,585 A | 8/1996 | Booth et al. | |
| 5,600,098 A | 2/1997 | Kazaks | |
| 5,674,752 A | 10/1997 | Buckley et al. | |
| 5,680,681 A | 10/1997 | Fuss | |

(56) References Cited

U.S. PATENT DOCUMENTS

| | | | |
|---|---|---|---|
| 5,691,062 A | 11/1997 | Shalaby et al. | |
| 5,701,370 A | 12/1997 | Muhs et al. | |
| 5,730,145 A | 3/1998 | Defares et al. | |
| 5,747,101 A | 5/1998 | Booth et al. | |
| 5,749,365 A | 5/1998 | Magill | |
| 5,760,340 A | 6/1998 | Orr, Jr. et al. | |
| 5,763,058 A | 6/1998 | Isen et al. | |
| 5,769,755 A | 6/1998 | Henry et al. | |
| 5,773,762 A | 6/1998 | Orr, Jr. et al. | |
| 5,774,341 A | 6/1998 | Urbish et al. | |
| 5,786,977 A | 7/1998 | Cohen | |
| 5,788,528 A | 8/1998 | Orr, Jr. et al. | |
| 5,798,907 A | 8/1998 | Janik | |
| 5,802,607 A | 9/1998 | Triplette | |
| 5,824,996 A | 10/1998 | Kochman et al. | |
| 5,829,987 A | 11/1998 | Fritsch et al. | |
| 5,831,198 A * | 11/1998 | Turley et al. | 89/1.11 |
| 5,832,296 A | 11/1998 | Wang et al. | |
| 5,834,693 A | 11/1998 | Waddell et al. | |
| 5,837,624 A | 11/1998 | Sakaguchi et al. | |
| 5,876,430 A | 3/1999 | Shoberg et al. | |
| 5,883,364 A | 3/1999 | Frei et al. | |
| 5,906,004 A | 5/1999 | Lebby et al. | |
| 5,911,595 A | 6/1999 | Orr, Jr. et al. | |
| 5,912,653 A | 6/1999 | Fitch | |
| 5,913,830 A | 6/1999 | Miles | |
| 5,914,585 A | 6/1999 | Grabon | |
| 5,914,660 A | 6/1999 | Mesibov et al. | |
| 5,919,141 A | 7/1999 | Money et al. | |
| 5,926,144 A | 7/1999 | Bolanos et al. | |
| 5,928,157 A | 7/1999 | O'Dwyer | |
| 5,931,764 A | 8/1999 | Freeman et al. | |
| 5,970,921 A | 10/1999 | Fulton | |
| 5,989,120 A | 11/1999 | Truchsess | |
| 5,995,077 A | 11/1999 | Wilcox et al. | |
| 5,997,983 A | 12/1999 | Caron et al. | |
| 6,023,372 A | 2/2000 | Spitzer et al. | |
| 6,024,575 A | 2/2000 | Ulrich | |
| 6,026,512 A | 2/2000 | Banks | |
| 6,047,203 A | 4/2000 | Sackner et al. | |
| 6,080,690 A | 6/2000 | Lebby et al. | |
| 6,083,156 A | 7/2000 | Lisiecki | |
| 6,097,607 A | 8/2000 | Carroll et al. | |
| 6,105,624 A | 8/2000 | Wildeman et al. | |
| 6,117,554 A | 9/2000 | Shalaby et al. | |
| 6,121,171 A | 9/2000 | Takahashi et al. | |
| 6,121,547 A | 9/2000 | Harada | |
| 6,126,572 A | 10/2000 | Smith | |
| 6,128,004 A | 10/2000 | McDowall et al. | |
| 6,135,951 A | 10/2000 | Richardson et al. | |
| 6,137,675 A * | 10/2000 | Perkins | 361/679.03 |
| 6,145,551 A | 11/2000 | Jayaraman et al. | |
| 6,210,771 B1 | 4/2001 | Post et al. | |
| 6,231,516 B1 | 5/2001 | Keilman et al. | |
| 6,253,099 B1 | 6/2001 | Oskin et al. | |
| 6,254,548 B1 | 7/2001 | Ishikawa et al. | |
| 6,254,551 B1 | 7/2001 | Varis | |
| 6,270,466 B1 | 8/2001 | Weinstein et al. | |
| 6,277,080 B1 | 8/2001 | Nissila et al. | |
| 6,295,466 B1 | 9/2001 | Ishikawa et al. | |
| 6,306,088 B1 * | 10/2001 | Krausman et al. | 600/301 |
| 6,315,009 B1 | 11/2001 | Jayaraman et al. | |
| 6,319,015 B1 * | 11/2001 | Faunce | 439/37 |
| 6,324,053 B1 | 11/2001 | Kamijo | |
| 6,325,066 B1 | 12/2001 | Hughes et al. | |
| 6,341,504 B1 | 1/2002 | Istook | |
| 6,341,550 B1 | 1/2002 | White | |
| 6,350,129 B1 | 2/2002 | Gorlick | |
| 6,360,406 B1 * | 3/2002 | Patterson et al. | 24/457 |
| 6,381,482 B1 | 4/2002 | Jayaraman et al. | |
| 6,385,473 B1 | 5/2002 | Haines et al. | |
| 6,413,225 B1 | 7/2002 | Sackner et al. | |
| 6,416,471 B1 | 7/2002 | Kumar et al. | |
| 6,420,008 B1 | 7/2002 | Lewis et al. | |
| 6,445,940 B1 | 9/2002 | Gevins et al. | |
| 6,461,307 B1 | 10/2002 | Kristbjarnarson et al. | |
| 6,463,310 B1 | 10/2002 | Swedlow et al. | |
| 6,474,367 B1 | 11/2002 | Jayaraman et al. | |
| 6,493,933 B1 | 12/2002 | Post et al. | |
| 6,494,829 B1 | 12/2002 | New, Jr. et al. | |
| 6,496,695 B1 | 12/2002 | Kouji et al. | |
| 6,522,531 B1 | 2/2003 | Quintana et al. | |
| 6,527,711 B1 | 3/2003 | Stivoric et al. | |
| 6,551,252 B2 | 4/2003 | Sackner et al. | |
| 6,561,987 B2 | 5/2003 | Pail | |
| 6,677,858 B1 | 1/2004 | Faris et al. | |
| 6,687,523 B1 | 2/2004 | Jayaramen et al. | |
| 6,727,197 B1 | 4/2004 | Wilson et al. | |
| 6,729,025 B2 | 5/2004 | Farrell et al. | |
| 6,743,030 B2 * | 6/2004 | Lin et al. | 439/131 |
| 6,767,218 B2 | 7/2004 | Marmaropoulos | |
| 6,783,498 B2 | 8/2004 | Sackner et al. | |
| 6,785,144 B1 | 8/2004 | Akram | |
| 6,854,988 B2 * | 2/2005 | Marmaropoulos et al. | 439/110 |
| 6,895,261 B1 * | 5/2005 | Palamides | 455/575.6 |
| 6,936,011 B2 | 8/2005 | Sheldon | |
| 6,941,775 B2 | 9/2005 | Sharma | |
| 6,970,731 B1 | 11/2005 | Jayaraman et al. | |
| 7,020,508 B2 | 3/2006 | Stivoric et al. | |
| 7,041,062 B2 | 5/2006 | Friedrichs et al. | |
| 7,076,291 B2 | 7/2006 | Pulkkinen et al. | |
| 7,092,846 B2 | 8/2006 | Vock et al. | |
| 7,265,970 B2 * | 9/2007 | Jordan | 361/679.27 |
| 7,319,895 B2 | 1/2008 | Klefstad-Sillonville et al. | |
| 7,559,902 B2 | 7/2009 | Ting et al. | |
| 7,618,260 B2 * | 11/2009 | Daniel et al. | 439/37 |
| 7,731,517 B2 | 6/2010 | Lee et al. | |
| 7,878,030 B2 * | 2/2011 | Burr | 66/173 |
| 7,881,051 B2 * | 2/2011 | Kim | 361/679.31 |
| 7,980,867 B2 * | 7/2011 | Dei Rossi et al. | 439/131 |
| 8,029,300 B2 * | 10/2011 | Finney et al. | 439/136 |
| 8,086,421 B2 | 12/2011 | Case et al. | |
| 8,200,323 B2 | 6/2012 | DiBenedetto et al. | |
| 2002/0032388 A1 | 3/2002 | Kristbjarnarson et al. | |
| 2002/0044059 A1 | 4/2002 | Reeder et al. | |
| 2002/0107451 A1 | 8/2002 | Pulkkinen et al. | |
| 2002/0124295 A1 * | 9/2002 | Fenwick et al. | 2/69 |
| 2003/0139680 A1 | 7/2003 | Sheldon | |
| 2004/0092186 A1 | 5/2004 | Wilson-Nguyen et al. | |
| 2004/0097823 A1 | 5/2004 | Friedrichs et al. | |
| 2004/0209396 A1 | 10/2004 | Krulevitch et al. | |
| 2004/0224138 A1 | 11/2004 | Farrell et al. | |
| 2004/0225199 A1 | 11/2004 | Evanyk et al. | |
| 2005/0054941 A1 | 3/2005 | Ting et al. | |
| 2005/0113655 A1 | 5/2005 | Hull | |
| 2005/0119586 A1 | 6/2005 | Coyle et al. | |
| 2005/0227811 A1 * | 10/2005 | Shum et al. | 482/1 |
| 2005/0240087 A1 | 10/2005 | Keenan et al. | |
| 2006/0009697 A1 | 1/2006 | Banet et al. | |
| 2006/0036142 A1 | 2/2006 | Brister et al. | |
| 2006/0117805 A1 | 6/2006 | Valentine et al. | |
| 2007/0105404 A1 * | 5/2007 | Lee et al. | 439/37 |
| 2007/0115259 A1 * | 5/2007 | Pai | 345/163 |
| 2007/0118043 A1 | 5/2007 | Oliver et al. | 600/519 |
| 2007/0279852 A1 * | 12/2007 | Daniel et al. | 361/683 |
| 2007/0299325 A1 * | 12/2007 | Farrell et al. | 600/301 |
| 2008/0000304 A1 | 1/2008 | Nagle et al. | |
| 2008/0015454 A1 * | 1/2008 | Gal | 600/509 |
| 2008/0139894 A1 | 6/2008 | Szydio-Moore et al. | |
| 2008/0188353 A1 | 8/2008 | Vitolo et al. | |
| 2008/0191106 A1 * | 8/2008 | Shiffler et al. | 248/188.9 |
| 2008/0205006 A1 * | 8/2008 | Fursich et al. | 361/726 |
| 2009/0102678 A1 * | 4/2009 | Mazza et al. | 340/693.9 |
| 2009/0105567 A1 | 4/2009 | Smith et al. | |
| 2009/0131759 A1 * | 5/2009 | Sims et al. | 600/301 |
| 2009/0190713 A1 * | 7/2009 | Wai | 377/24.2 |
| 2011/0251469 A1 * | 10/2011 | Varadan | 600/301 |
| 2011/0275940 A1 * | 11/2011 | Nims et al. | 600/483 |
| 2011/0295083 A1 * | 12/2011 | Doelling et al. | 600/301 |

FOREIGN PATENT DOCUMENTS

| | | |
|---|---|---|
| EP | 1 064 963 A1 | 1/2001 |
| EP | 1 077 044 A1 | 2/2001 |

(56) References Cited

FOREIGN PATENT DOCUMENTS

| | | |
|---|---|---|
| EP | 1 164 815 A1 | 12/2001 |
| EP | 1 234 903 A1 | 8/2002 |
| EP | 1 328 137 A2 | 7/2003 |
| EP | 1 330 964 A2 | 7/2003 |
| EP | 1 339 259 A1 | 8/2003 |
| EP | 1 444 907 A1 | 8/2004 |
| EP | 1 269 502 B1 | 6/2005 |
| EP | 1 021 064 B1 | 9/2005 |
| EP | 1 049 354 B1 | 12/2005 |
| EP | 1 201 806 B1 | 12/2005 |
| FR | 2 836 050 A1 | 2/2003 |
| FR | 2858758 A2 | 8/2003 |
| GB | 2 143 135 A | 2/1985 |
| GB | 2 331 631 A | 2/1999 |
| GB | 2 336 514 A | 10/1999 |
| GB | 2 378 054 A | 1/2003 |
| GB | 2 385 277 A | 8/2003 |
| GB | 2 386 339 A | 9/2003 |
| GB | 2 396 256 A | 6/2004 |
| WO | WO 98/20200 | 5/1998 |
| WO | WO 99/19019 | 4/1999 |
| WO | WO 99/64657 | 12/1999 |
| WO | WO 00/25193 | 5/2000 |
| WO | WO 01/78577 A2 | 10/2001 |
| WO | WO 01/88935 | 11/2001 |
| WO | WO 02/07816 | 1/2002 |
| WO | WO 02/45538 A2 | 6/2002 |
| WO | WO 02/060370 A2 | 8/2002 |
| WO | WO 02/087929 A1 | 11/2002 |
| WO | WO 02/095839 A2 | 11/2002 |
| WO | WO 03/039417 A2 | 5/2003 |
| WO | WO 03/052541 A2 | 6/2003 |
| WO | WO 03/072861 A1 | 9/2003 |
| WO | WO 03/094717 A1 | 11/2003 |
| WO | WO 2004/053638 A2 | 6/2004 |
| WO | WO 2004/064108 A2 | 7/2004 |
| WO | WO 2004/091503 A2 | 10/2004 |
| WO | WO 2004/098703 A2 | 11/2004 |
| WO | WO 2004/107831 A2 | 12/2004 |
| WO | WO 2004/114401 A2 | 12/2004 |
| WO | WO 2005/000052 A1 | 1/2005 |
| WO | WO 2005/011415 A1 | 2/2005 |
| WO | WO 2005/013738 A2 | 2/2005 |
| WO | WO 2008039082 A2 * | 4/2008 |

OTHER PUBLICATIONS

Mathews, R. et al; "A Wearable Physiological Sensor Suite for Unobtrusive Monitoring of Physiological and Cognitive State", Proceedings of the 29th Annual International Conference of the IEEE EMBS Cité Internationale, Lyon, France Aug. 23-26, 2007, p. 1-6.*

Axisa, F. et al, "Flexible Technologies and Smart Clothing for Citizen, Medicine, Home Healthcare, and Disease Prevention", IEE transactions on Information Technology in biomedicine, vol. 9, No. 3, Sep. 2005, p. 325-336.*

Pandian, P.S. et al; "Wireless Sensor Network for Wearable Physiological Monitoring"; Journal of Networks, vol. 3, No. 5, May 2008, p. 21-29.*

Written opinion of the International Searching Authority for International Application No. PCT/US2011/01331 Dec. 15, 2011, seven (7) pages, unnumbered.

U.S. Appl. No. 12/799,822, filed Nov. 3, 2011, Richard B. Streeter.

U.S. Appl. No. 12/804,962, filed Feb. 9, 2010, Mielcarz et al.

U.S. Appl. No. 12/924,241, filed Mar. 29, 2010, McDonald et al.

Gemperie, Francine, Kasabach, Chris, Stivoric, John, Bauer, Malcolm and Martin, Richard, *Design for Wearability*, Institute for Complex Engineered Systems, Carnegie Mellon University, Pittsburgh, PA http://www.ices.emu.edu/desiqn/weability 1998 (7 pages).

"E-broidery: Design and Fabrication of Textile-based Computing", by E.R. Post et al., IBM Systems Journal, vol. 39, Nos. 3 & 4, 2000, pp. 840-860.

"Intrabody Buses for Data and Power", E. Rhemi Post et al., MIT Media Laboratory, 1997 IEEE, pp. 52-55.

Landon, Chris, Respiratory Monitoring: Advantages of Inductive Plethysmography over Impedance Pneumography, a whitepaper published by VivoMetrics, date unknown, pp. 1-7.

E. Rehmi Post and Maggie Orth, Smart Fabric, or "Wearable Clothing", The MIT Media Laboratory, pp. 167-168 of the Digest of Papers of the First IEEE International Symposium on Wearable Computers, Oct. 13-14, 1997 held in Cambridge, Massachusetts.

"Wearable Sensor Badge & Sensor Jacket for Context Awareneess", Farringdon et al., Philips Research Laboratories, Surrey, U.K., 1999, IEEE pp. 107-113.

"Electronic Suspenders: A Fabric Power bus and Data Network for Wearable Digital Devices", Michael M. Gorlick, The Aerospace Corporation, El Segundo, California, 1999, IEEE, pp. 114-121.

Harper, Charles A., Handbook of Plastics, Elastomers, and Composites, Third Edition, McGraw-Hill, New York, 1996, pp. 6.14-6.19 (4 pages).

Neuman, Michael R., Biopotential Electrodes. The Biomedical Engineering Handbook, vol. 1, edited by Joseph D. Bronzino, CRC Press, Boca Raton, FL, 2000, pp. 48-1-48-12.

Post, E. Rhemi and Maggie Orth, Smart Fabric, or Washable Computing, the MIT Media Laboratory, Digest of Papers of the first IEEE International Symposium on Wearable Computers, Oct. 13-14, 1997 held in Cambridge, Massachusetts (4 pages).

Zephyr Biotechnology, Zephyr BioHarness, www.zephyrtechnology.com (2 pages).

* cited by examiner

*FIG. 1*

PRIOR ART

*FIG. 2*

PRIOR ART

PHYSIOLOGICAL STATUS MONITORING SYSTEM

RELATED APPLICATIONS

This application is related to U.S. patent application Ser. No. 11/807,449, filed on May 29, 2007 and U.S. patent application Ser. No. 10/922,336, filed Aug. 20, 2004, both of which are incorporated herein by reference.

FIELD OF THE INVENTION

The subject invention relates to a physiological monitoring system able to monitor and record a person's vital signs such as respiration, heart rate, and the like.

BACKGROUND OF THE INVENTION

Various systems are known which monitor a person's heart rate, respiration rate, body temperature, and the like. For ambulatory-type systems, a portable unit may be used to wirelessly transmit the various sensor signals to a base station computer for processing, display, and storage.

For sport, outdoor, and military applications especially, the portable unit must be waterproof and removable from the shirt or garment carrying the sensors in order to wash the shirt or garment. The electrical connections between the sensors and the portable unit must be robust. And yet, no system will be commercially viable if numerous manual labor steps are required increasing manufacturing costs. The portable unit must be small, remain electrically connected to the sensors while in use, and not interfere with the activity being carried out by the user.

Several wearable physiological monitoring systems have been proposed. They typically include one or more sensors (e.g., a respiration sensor, a heart rate sensor, an accelerometer, and the like). Using a transmitter, the sensed data is transmitted to a base/readout unit. Some prior art references disclose a sensor subsystem with a transmitter apparently hard wired to the sensors. See, e.g., U.S. Published Patent Application No. 2005/0240087 and U.S. Pat. No. 6,416,471, incorporated herein by this reference.

Other prior art references disclose a stand alone sensor/transmitter unit carried by the user. See, e.g., U.S. Pat. No. 7,092,846. Such systems cannot sense respiration, heart rate, and the like. The Apple+Nike product, now on the market, is similar.

For sports, military, and other applications where the sensor subsystem is integrated into a shirt or other garment, the garment is typically washed between uses. Also, when worn, it is important that nothing interfere with the user's comfort. Some physiological monitoring systems are not comfortable to wear; others are difficult to use. Some require preparation prior to and/or after donning the garment. Some include discrete wires which must be routed and/or connected each time the garment is worn. Some include electrodes which must be secured to the person's body and/or must be used in connection with a conductive gel. Some physiological monitoring garments are simply not aesthetically pleasing. Others interfere with the activities of and duties carried out by the wearer.

BRIEF SUMMARY OF THE INVENTION

In accordance with one aspect of the subject invention, a new physiological monitoring system is provided which, in one specific version, is more ergonomic than prior systems. Various other embodiments are within the scope of the subject invention.

The subject invention features, in one example, a physiological monitoring system comprising a garment such as a shirt, a band integrated with the garment including respiration sensing conductors and one or more additional conductors, and a heart rate sensor integral with the garment electrically connected to an additional conductor. A dock is attached to the garment and includes a receptacle comprising a printed circuit board including an accelerometer and a first connector component electrically connected to said respiration sensing conductors and the additional conductor(s) and a cover over said printed circuit board. A housing is attached to the garment and receives the receptacle therein. A portable transmitting unit is removeably received in the dock and includes a second connector component mateable with the first connector component. The portable transmitting unit is configured to wirelessly transmit respiration, heart rate, and accelerometer data to a base unit.

Padding may be included behind the receptacle and/or over the housing for comfort. Preferably, the housing has a concave shape. Fasteners may secure the receptacle inside the housing. One preferred housing includes a tongue member and side rails upstanding therefrom receiving the portable transmitting unit therebetween. Typically, the rails curve inwardly over the tongue member. Also, the portable transmitting unit may include a latch mechanism releasably engaging the portable transmitting unit in the housing. The latch mechanism may include spaced spring loaded fingers releasably received in indentations in the housing.

In one version, the dock with the portable transmitting unit received therein is no larger than 8 inches wide, 4 inches long, and 3 inches high.

The second connector component may include pogo pins and then the first connector component includes conductors for the pogo pins. A seal member may be included about the first connector component. Typically, the cover is sewn and/or glued to the band. A typical portable transmitting unit further includes a printed circuit board, a battery under the printed circuit board, and an antenna over the printed circuit board acting as a ground plane for the antenna.

The subject invention also features a physiological monitoring system comprising a sensor subsystem worn by a person including at least a heart rate sensor, a dock associated with the sensor subsystem including a first connector component electrically connected to the heart rate sensor, and a portable transmitting unit received in the dock including a transmitter and a connector component removeably mateable with the dock connector component to route heart rate data to the transmitter. The preferred sensor subsystem includes a flexible band integrated with a shirt including at least one conductor extending between the heart rate sensor and the dock. The band may include a pair of conductors configured for sensing respiration.

One typical physiological monitoring system in accordance with the subject invention features a sensor subsystem worn by a person including at least one sensor (e.g., a heart rate sensor). A dock is associated with the sensor subsystem and includes a receptacle comprising a printed circuit board including a dock connector component electrically connected to the sensor and a cover over the printed circuit board, and a housing receiving the receptacle therein. A portable transmitting unit is received in the dock and includes a transmitter and a connector component removeably mateable with the dock connector component to route sensor data to the transmitter.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
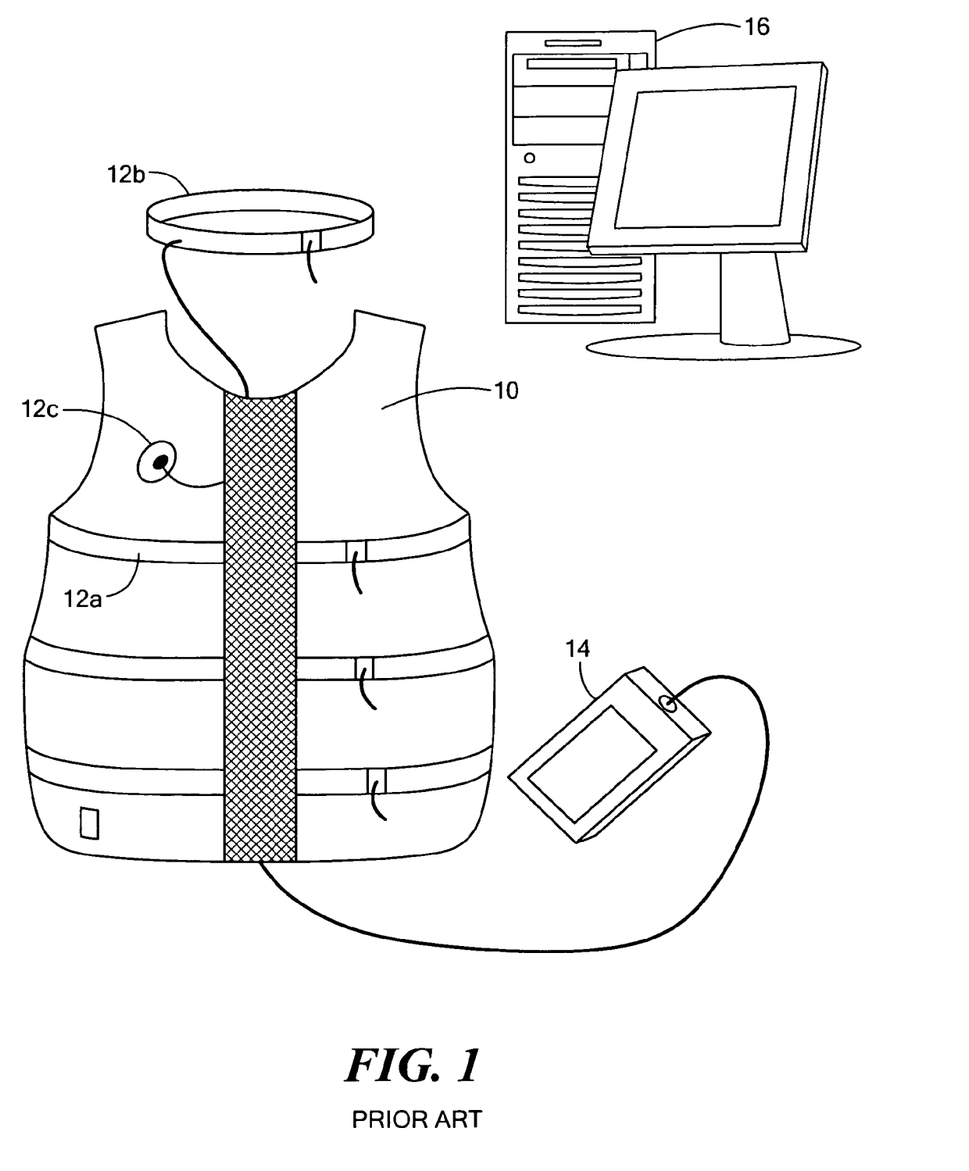
FIG. 1 is a schematic front view showing an example of one prior art physiological monitoring system.
Figure 2:
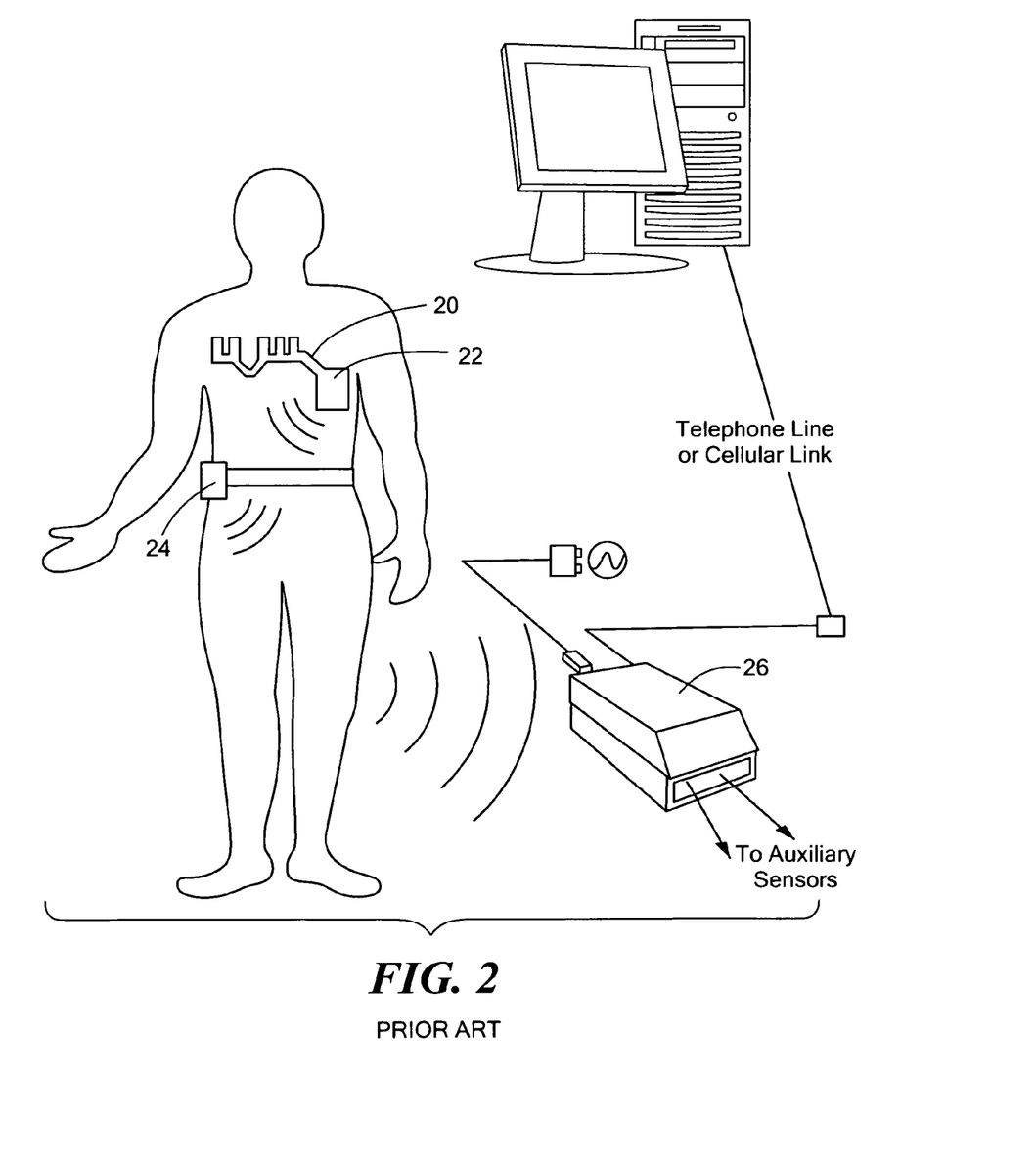
FIG. 2 is a highly schematic view showing another example of a prior art physiological monitoring system.

FIG. 1 shows a garment 10 in accordance with U.S. Pat. No. 6,783,498 with sensors 12a, 12b, 12c and the like apparently hardwired to electronic unit 14 which transmits signals to base unit 16. FIG. 2 shows a disposable sensor band 20 described in U.S. Pat. No. 6,416,471 including a transmitter 22 which transmits signals to signal transfer unit 24 which itself relays those signals to base station 26.

As discussed in the background section above, such systems are not particularly suited for sports, outdoor activities, or military applications. A soccer player or basketball player, for example, would not be willing to carry or wear the electronic units associated with these prior art systems.

Figure 3:
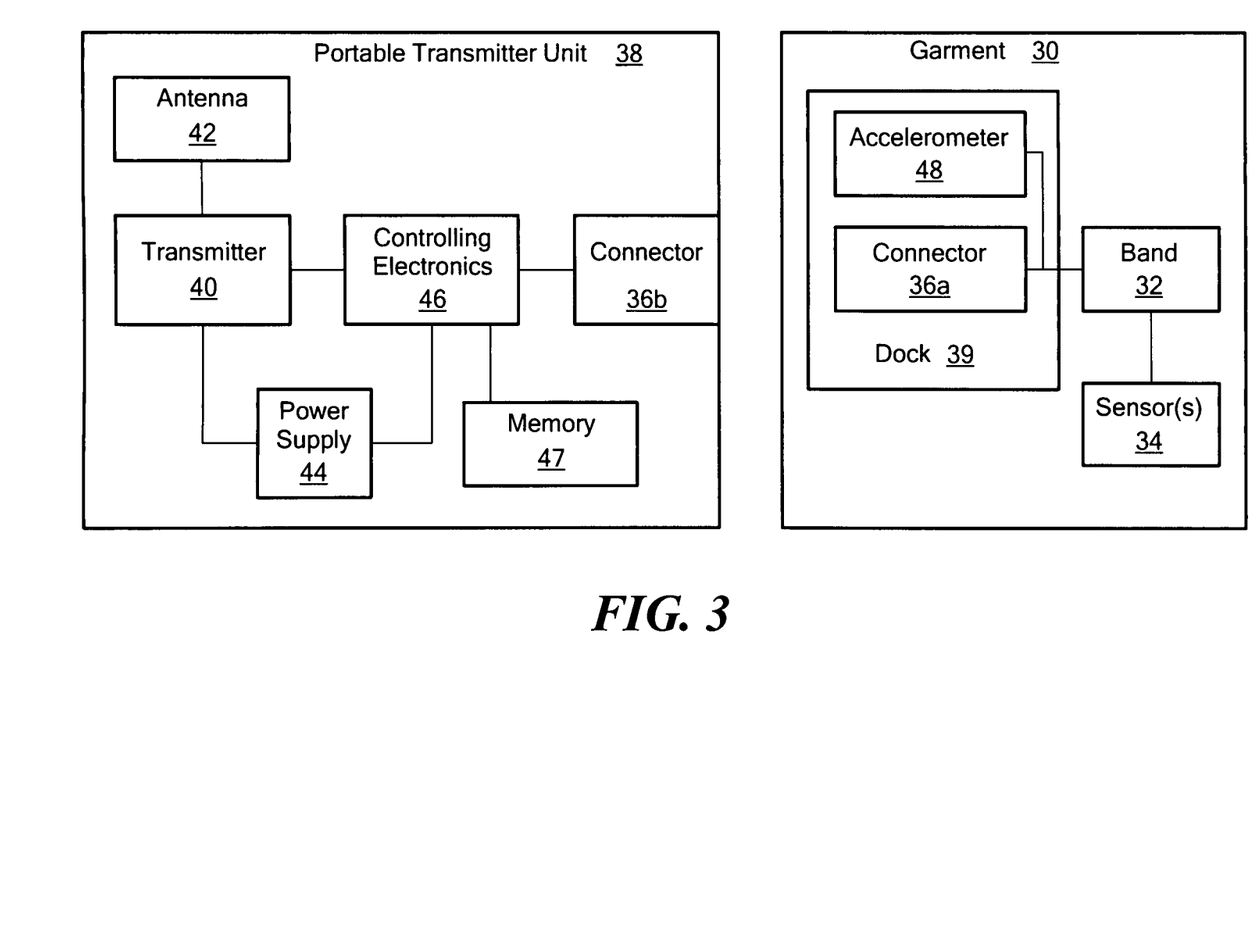
FIG. 3 is a block diagram depicting the primary components associated with an example of a physiological monitoring system in accordance with the subject invention.

A new physiological monitoring system in accordance with the subject invention features, in one example, a garment (e.g., a shirt) 30, FIG. 3 including a band 32 associated therewith. The band may include sensing means and/or may be attached and/or electrically connected to one or more sensors 34. See U.S. patent application Ser. No. 11/807,449 incorporated herein by this reference. The band includes conductors which are connected to connector 36a of dock 39. Dock 39 typically includes accelerometer 48. Accelerometer 48 is included to provide data indicative of the users speed and/or the load experienced by the user. Connector 36a may include conductive pads, for example.

Portable transmitting unit 38, removeably received in dock 39, includes connector 36b which mates with connector 36a of dock 39 to receive the signals transmitted by the conductors in band 32 and the signals from accelerometer 48. Connector 36b may include pogo pins, for example, which mate with the conductive pads of connector 36a when portable transmitting unit 38 is located in dock 39. Portable transmitting unit 38 is configured to wirelessly transmit signals via transmitter 40 and antenna 42 to a base unit or the like. Performance data can be stored in memory 47 for later transmission. Portable transmitting unit 38 is typically small, has a low profile, and is removed from the garment so that the garment can be washed. Portable transmitting unit 38 also typically includes power supply 44 providing power to transmitter 40 and controlling electronics 46 which receives and processes signals from connector 36b and controls transmitter 40 accordingly. Other signal processing components such as A/D converters, signal processing circuitry, and the like are not shown in FIG. 3.

Figure 4:
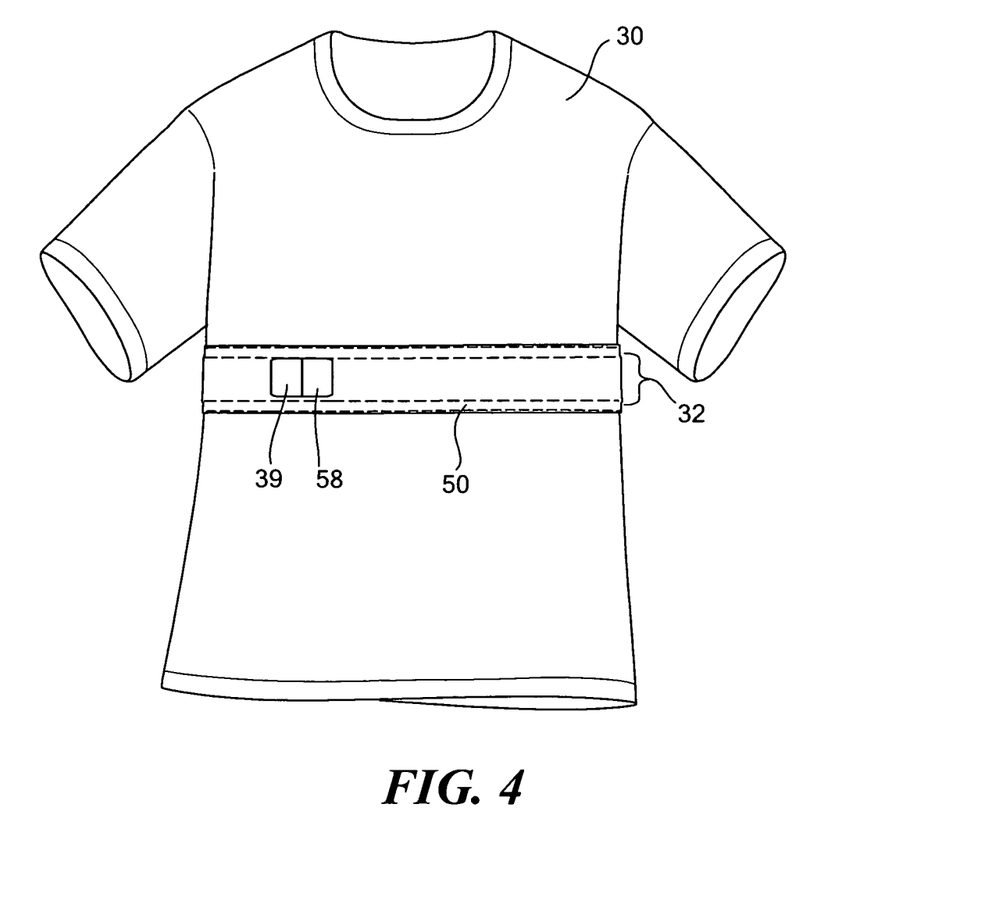
FIG. 4 is a schematic front view of an example of a physiological monitoring shirt in accordance with the subject invention.

An easily washable shirt 30, FIG. 4 can be made of any fabric (e.g., cotton) but typically is made of a "compression" fabric often including Lycra material (e.g., the POLARTEC® material available from Malden Mills). For additional comfort, moisture management and the like, shirt 30 may include fabric fibers of variable loft, thickness or density placed to coincide with preferred body locations where desired. Sewn or bonded to the inside (or outside) of this or any conventional shirt is a stretchable circumferential band the outline of which is shown in FIG. 4 at 32. The result in one version is a shirt free of any atypical seams or the like. The band includes an integrated respiration detection subsystem, sensors, signal transmission conductors for the sensors, and a connection subsystem. Cover 50, if used, also typically made of compression or plush material, may be sewn and/or bonded over the band. The band 32 may include an integrated respiration detection subsystem, one or more sensors, and signal transmission conductors for the sensors. Portable transmitting unit 38 is received in dock 39 attached to shirt 30. This electronics module wirelessly transmits respiration and other (e.g., ECG) physiological status signals to a remote unit where the wearer's ECG, respiration rate, skin temperature, heart rate, speed, and activity level or load may be displayed and/or recorded.

Figure 5:
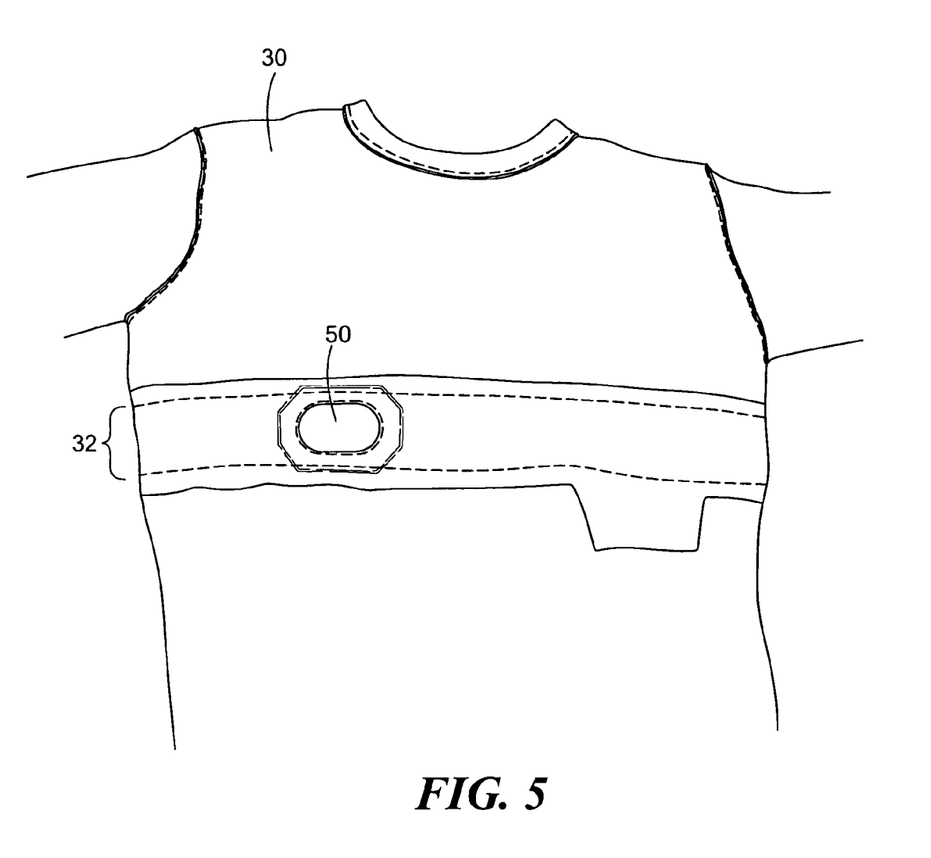
FIG. 5 is a schematic front view of the inside of the shirt shown in FIG. 4.

FIG. 5 shows the inside of shirt 30 and again the outline of the circumferential band can be seen at 32. FIG. 5 also shows one exposed ECG electrode 50a inside the shirt for monitoring the wearer's heart rate. Additional exposed ECG electrodes may be attached to band 32. See U.S. patent application Ser. No. 11/807,449. Other sensors may be added and may be integrated with the band or connected to it. Examples include thoracic bioimpedance sensors or biomechanical sensors, one or more temperature sensors connected to the signal transmission elements of the band.

Note the lack of any loose wires inside or outside the shirt. Other than the electrodes, and/or any sensors or an optional cover, only shirt material touches the wearer's skin. Except for electronics module 38, FIG. 4 and the slight outline of the band, shirt 30 looks just like a normal shirt. Shirt 34 is thus comfortable, aesthetically pleasing, quickly donnable and doffable, and easy to use. It can be worn under other clothing, it is easily cleaned, it can wick away body perspiration, and it does not interfere with the activities of or duties carried out by the wearer. Physiological parameters measured are more accurate because the portion of the shirt including the stretchable band can hold sensors in more intimate contact with the wearer's body. Also, the sensors are located away from the module so as the module moves with the movement of the wearer the sensors are not impacted, resulting in less motion artifact and further increased accuracy of measurements.

Figure 6:
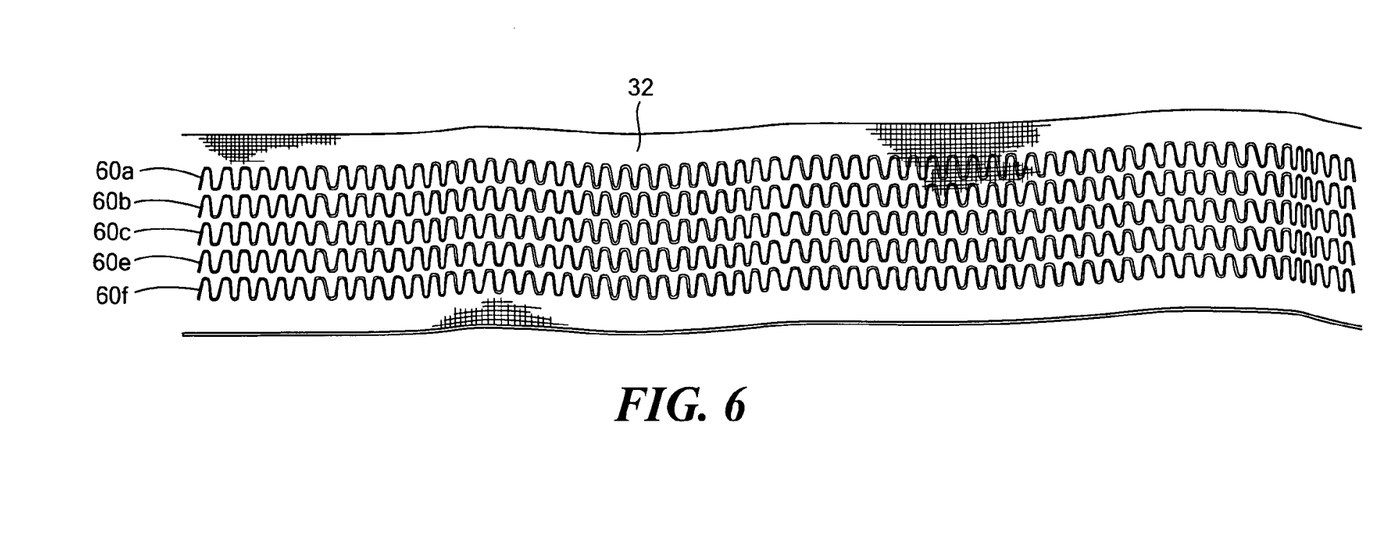
FIG. 6 is a schematic front top view of one embodiment of a stretchable band integrated into the shirt shown in FIGS. 4 and 5.

Stretchable band 32 is shown alone in FIG. 6. Integrated with the fabric of band 32 are conductors (typically insulated wires) in a flexible configuration typically in-plane nested pairs as shown at 60a-60f. The nested pairs may be sinusoidal as shown, or any other suitable configuration such as triangle wave or zig-zag (not shown). One conductor pair 60a is shown more clearly in FIGS. 7A-7B and can be used as a component of a respiration sensing subsystem. When the band is relaxed because the wearer has exhaled, the distance between wires 70a and 70b is $d_1$, FIG. 7A. When the band is stretched because the wearer has inhaled, the distance between wires 70a and 70b is $d_2$, FIG. 7B. In this way, by configuring band 32, FIG. 6 to be circumferential about the wearer's chest and snug thereabout in the relaxed configuration, when the wearer breathes, any nested conductor pair in the band can be used as a respiration detector.

Figure 7A:
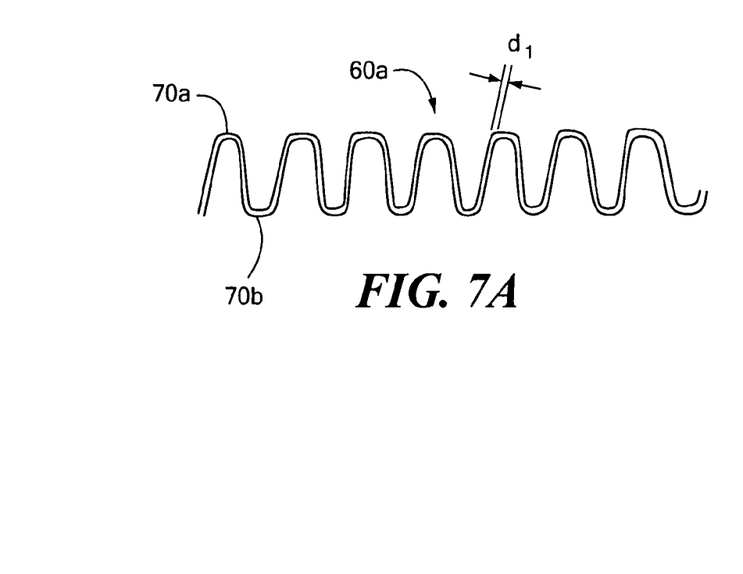
FIG. 7A is a highly schematic depiction showing conductors in the stretchable band of FIG. 6 when the band is in its relaxed state.
Figure 7B:
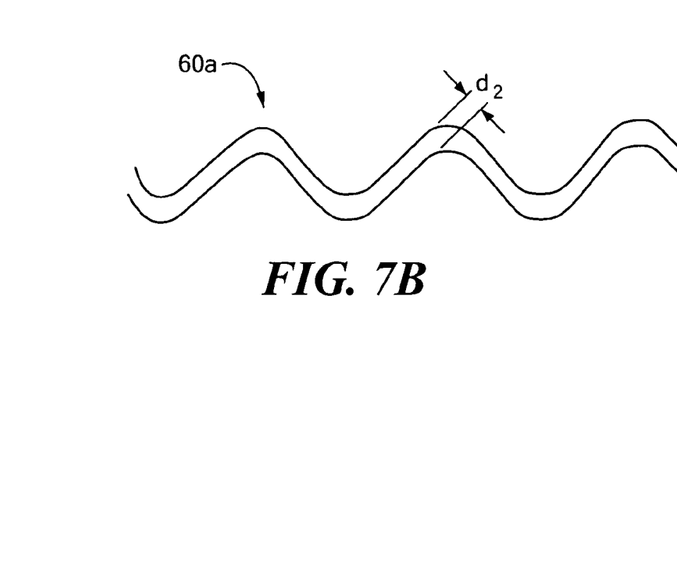
FIG. 7B is a highly schematic view similar to FIG. 7A except that now the distance between the conductors in the band has changed because the band is in its expanded state.

An electronics module includes a circuit which detects changes in, for example, capacitance as the adjacent nested circumferential conductors move away from and towards each other as stretchable band 32, FIG. 6 expands and contracts as shown in FIGS. 7A-7B. That change in impedance (e.g. capacitance) is thus indicative of respiration rate, indicating frequency of breaths taken by the wearer, as well as the depth or volume of each breath. In a plot of impedance and time, peak to peak distance is indicative of breathing rate or frequency.

Other conductor pairs can also be used for sensing respiration but typically at least a few conductors are reserved for signal transmission from sensors such as the ECG electrodes to an electronics module and possibly between the electronics module and these and other sensors or processing units which may be included on or electrically connected to the band.

Figure 8:
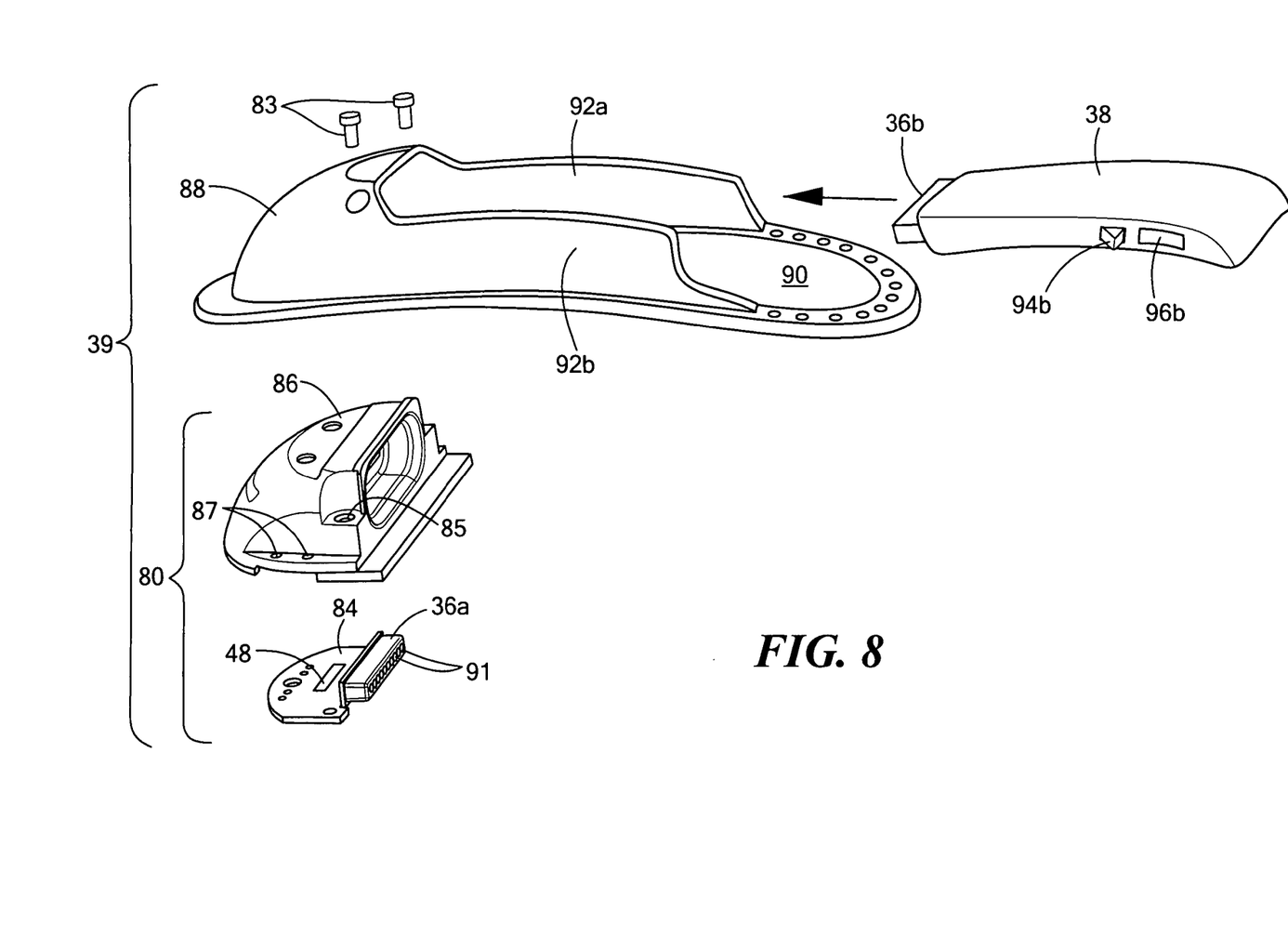
FIG. 8 is a schematic exploded front view showing the primary components associated with an example of a docking station attached to the shirt shown in FIGS. 4 and 5 for a portable transmitting unit shown.

FIG. 8 shows an example of dock 39 which is attached to shirt 30, FIG. 4. Dock 39 includes receptacle 80 which includes printed circuit board 84 encapsulated (potted) in cover 86. Cover 86 is secured (e.g., sewn and/or glued) to band 32, FIGS. 4-6. Holes 87 can be used to sew cover 86 to the band. Conductors in the band and/or conductors connected those conductors extend through board 84 where they may be sealed against water ingress and then routed to connector 36a. Connector 36a may include conductive pads 91 or female connectors, or the like. Board 84 may also includes accelerometer 48 (typically a three axis accelerometer) the output of which is routed via printed circuit board 84 to connector 36a. Associating accelerometer 48 with dock 39 instead of portable transmitting unit 38 has several advantages. Dock 39 moves in a way more closely related to the user's movements. Also, portable transmitting unit 38 can now be made smaller, and it is rendered less expensive and less complex.

Dock 39 can be attached at any location on the garment and stretchable bands are used to electrically connect dock 39 to sensors located elsewhere on the garment and/or to a respiration sensing band as disclosed above. Cover 86 may be sealed (e.g., ultrasonically welded) to board 84. Fasteners 83 secure cover 86 to housing 88 via bosses (e.g., boss 85) in cover 86.

Figure 9:
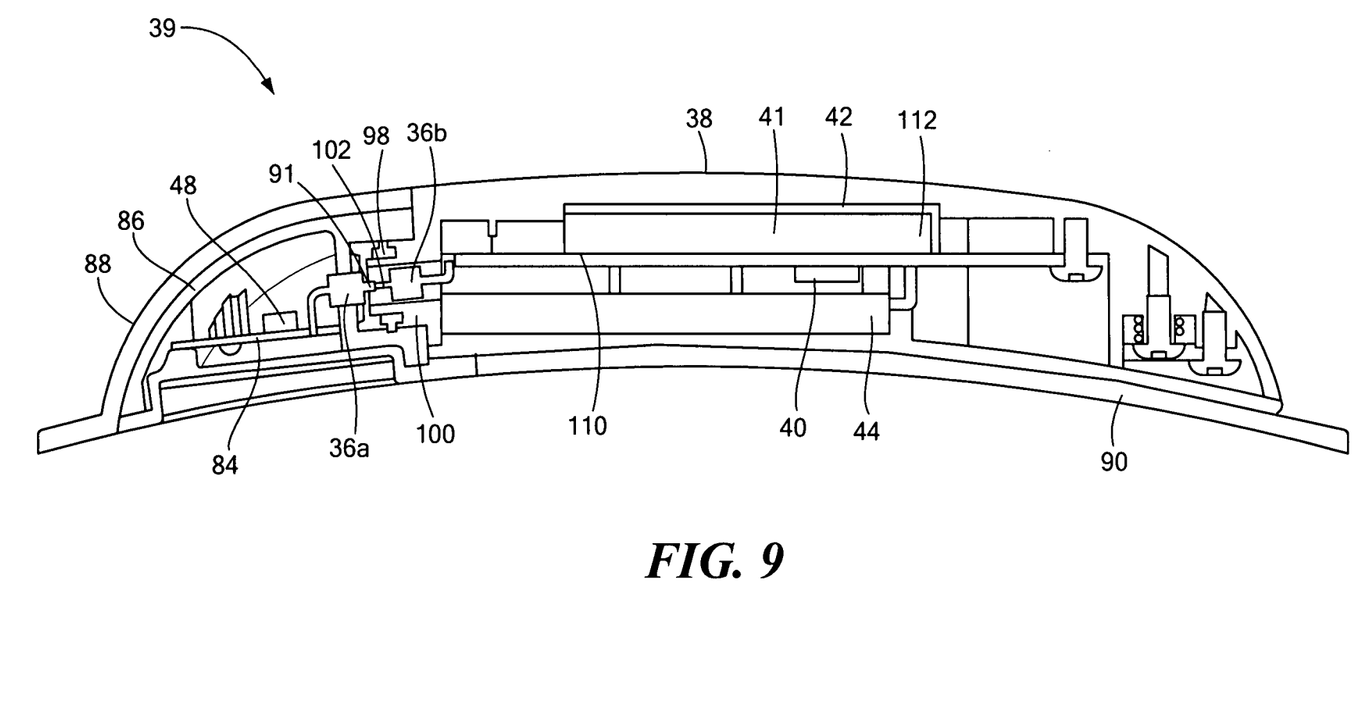
FIG. 9 is a schematic cross-sectional side view of a portable transmitting unit in accordance with the subject invention inserted into the docking station on the garment.

Housing 88 is attached (e.g., sewn and/or glued) to shirt 30, FIG. 4 and receives the portable transmitting unit 38, FIGS. 8-9 therein. Portable transmitting unit 38 includes connector 36b which mates with connector 36a of dock 39 when portable transmitting unit 38 is slid into dock 39. In this way, the portable transmitting unit receives respiration, heart rate, and accelerometer data from the shirt and records the data via memory 47, FIG. 3 and/or transmits it to a base station for the monitoring of a person wearing the shirt (e.g., by a coach, trainer, commander, or the like) via transmitter 40. The components shown in FIG. 8-9 may be made of plastic.

In this preferred example, housing 88 includes tongue member 90, FIGS. 8-9 and side rails 92a and 92b, FIG. 8 upstanding from tongue member 90 receiving portable transmitting unit 38, FIGS. 8-9 therebetween. Rails 92a and 92b, FIG. 8 curve inwardly over tongue member 90 to retain the portable transmitting unit in place forming a dovetail-like interlock between the portable transmitting unit and the dock. Portable transmitting unit 38, FIG. 10 also includes a latch mechanism engaging the portable transmitting unit in housing 88. The latching mechanism shown in FIG. 10 includes spaced spring loaded fingers 93a and 93b releasably received in indents 94a and 94b, respectively, in housing 88. Buttons 96a and 96b, when pushed, disengage fingers 93a and 93b from indents 94a and 94b to allow portable transmitting unit 38 to be removed from housing 88.

When portable transmitting unit 38 is in housing 88, the combination is typically no larger than 4 inches wide, 8 inches long, and 3 inches high. A prototype unit measured 4 inches long, 2 inches wide and 0.6 inches high. As shown in both FIGS. 8 and 9, housing 88 has a concave conforming shape and portable transmitting unit 38 is shaped to fit the shape of the housing. The result is a low profile, small, conforming unit which can be used by athletes, soldiers, or even animals. Padding may be added behind substrate 82 as well as over housing 88 for additional comfort and safety.

O-ring seal 98, FIG. 9 about connector 36b housing 100 of portable transmitting unit 38 helps insure a watertight connection between portable transmitting unit 38 and cover 86. Connector 36b typically includes pogo pins such as pogo pin 102 received in a port of connector 36a or otherwise disposed to contact a trace or pad associated with connector 36a or conductive element 91 as shown.

Figure 10:
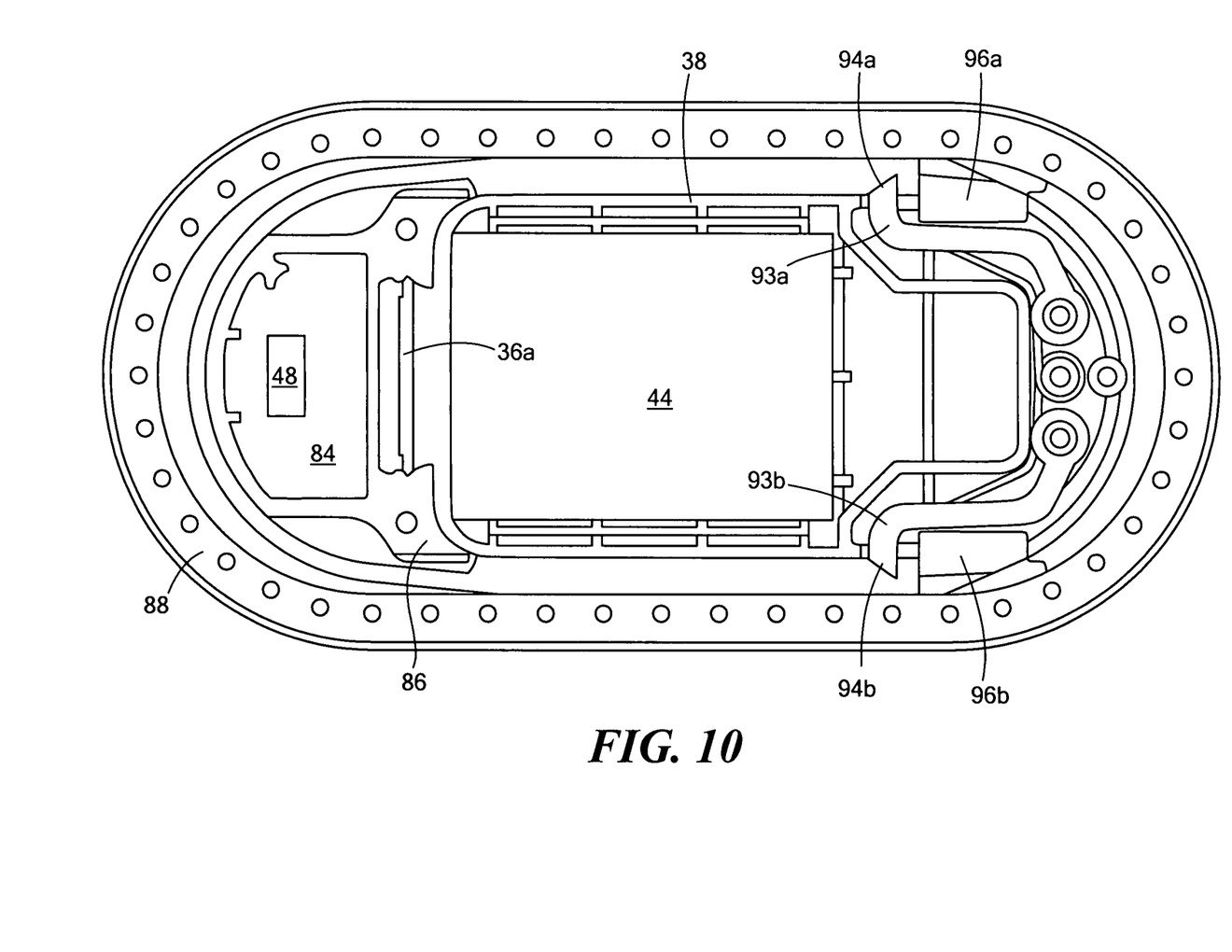
FIG. 10 is a schematic cross-sectional top view of the subassembly shown in FIG. 9.

FIGS. 9 and 10 also show portable transmitting unit 38 antenna 42, power supply (e.g., a lithium battery) 44, and main printed circuit board 110 (for controlling electronics 46 and transmitter 40, FIG. 3). Included may be a microprocessor for processing signals from the accelerometer, respirator, heart rate sensor, and any other sensors for transmission by the transmitter of portable transmitting unit 38. Double sided tape 41 may be placed between antenna 42 and printed circuit board 110. Transmitter 40 is also shown in FIG. 9 as is accelerometer 48. PCB 110 acts as a ground plane for the antenna and decouples the wearer's body from RF energy transmitted via antenna 42 increasing the transmission range. Battery 44 is behind antenna 42 so no RF energy is blocked. Preferably, no conductive components block antenna 42.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A physiological monitoring system comprising:
 a garment;
 a band integrated with the garment including respiration sensing conductors and one or more additional conductors;
 a heart rate sensor integral with the garment and electrically connected to a said additional conductor;
 a dock attached to the garment, the dock including:
  a receptacle comprising:
   a cover secured to the band,
   a printed circuit board within the cover and including an accelerometer and a first connector component electrically connected to said respiration sensing conductors and said additional conductor;
  an elongate housing attached to the garment and housing the receptacle in one end thereof; and
  a portable transmitting unit configured to be removably slid in the elongate housing and including a second connector component mateable with the first connector component, the portable transmitting unit configured to wirelessly transmit respiration, heart rate, and accelerometer data to a base unit.

2. The system of claim 1 further including padding behind the receptacle.

3. The system of claim 1 further including padding over the housing.

4. The system of claim 1 in which the housing has a concave shape.

5. The system of claim 1 further including fasteners securing the receptacle inside the housing.

6. The system of claim 1 in which the housing includes a flat tongue member and spaced side rails upstanding from opposing sides thereof receiving the portable transmitting unit therebetween.

7. The system of claim 6 in which the rails curve inwardly over the tongue member.

8. The system of claim 1 in which the portable transmitting unit includes a latch mechanism releasably engaging the portable transmitting unit in the housing.

9. The system of claim 8 in which said latch mechanism includes spaced spring loaded fingers releasably received in indentations in the housing.

10. The system of claim 1 in which the dock with the portable transmitting unit received therein is no larger than 4 inches wide, 8 inches long, and 3 inches high.

11. The system of claim 1 in which the second connector component includes pogo pins and the first connector component includes conductors for the pogo pins.

12. The system of claim 1 further including a seal member about the first connector component.

13. The system of claim 1 in which the cover is sewn and/or glued to the band.

14. The system of claim 1 in which the printed circuit board is potted in the cover.

15. The system of claim 1 in which the portable transmitting unit further includes a printed circuit board, a battery under the printed circuit board, and an antenna over the printed circuit board acting as a ground plane for the antenna.

* * * * *